United States Patent
Bernhardt et al.

(10) Patent No.: US 7,599,472 B2
(45) Date of Patent: Oct. 6, 2009

(54) METHOD, X-RAY TUBE AND IMAGING SYSTEM FOR ADJUSTING THE POSITION OF THE X-RAY TUBE FOCUS

(75) Inventors: Jens Bernhardt, Erlangen (DE); Andreas Meyer, Möhrendorf (DE); Anton Nekovar, Neunkirchen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/863,518

(22) Filed: Sep. 28, 2007

(65) Prior Publication Data
US 2008/0080664 A1 Apr. 3, 2008

(30) Foreign Application Priority Data
Sep. 29, 2006 (DE) .................. 10 2006 046 734

(51) Int. Cl.
*H01J 35/30* (2006.01)
(52) U.S. Cl. ..................... 378/137; 378/207
(58) Field of Classification Search ............... 378/16, 378/137, 138
See application file for complete search history.

(56) References Cited
U.S. PATENT DOCUMENTS
5,065,420 A * 11/1991 Levene .................. 378/137

6,658,085 B2 12/2003 Sklebitz
6,976,953 B1 * 12/2005 Pelc ......................... 600/411
2005/0265521 A1 * 12/2005 Deuringer et al. ......... 378/138
2006/0280293 A1 * 12/2006 Hardesty ................. 378/205

FOREIGN PATENT DOCUMENTS
DE 43 25 351 1/1995
DE 196 11 228 10/1997

OTHER PUBLICATIONS
Brochure for AXIOM Artis dFC Magnetic Navigation, Siemens Medical Solutions (2004).
"Imaging Systems for Medical Diagnostics," Oppelt, Chapter 12.1, "The X-ray Tube" (2005).

* cited by examiner

*Primary Examiner*—Edward J Glick
*Assistant Examiner*—Mona M Sanei
(74) *Attorney, Agent, or Firm*—Schiff Hardin LLP

(57) ABSTRACT

In order to reduce the influence of magnetic interference fields on the position of an x-ray focus of an x-ray tube, the deviation of a current focus position from a target focus position or of a measurement value proportional to the deviation is determined, the focus position by reducing the deviation of the current focus position from the target focus position, or the measurement value proportional to the deviation, on the basis of the determined deviation or the determined measurement value proportional to the deviation. The deviation of the current focus position from the target focus position or the measurement value proportional to the deviation is regulated to a value of essentially zero via repeated determination and correction.

7 Claims, 2 Drawing Sheets

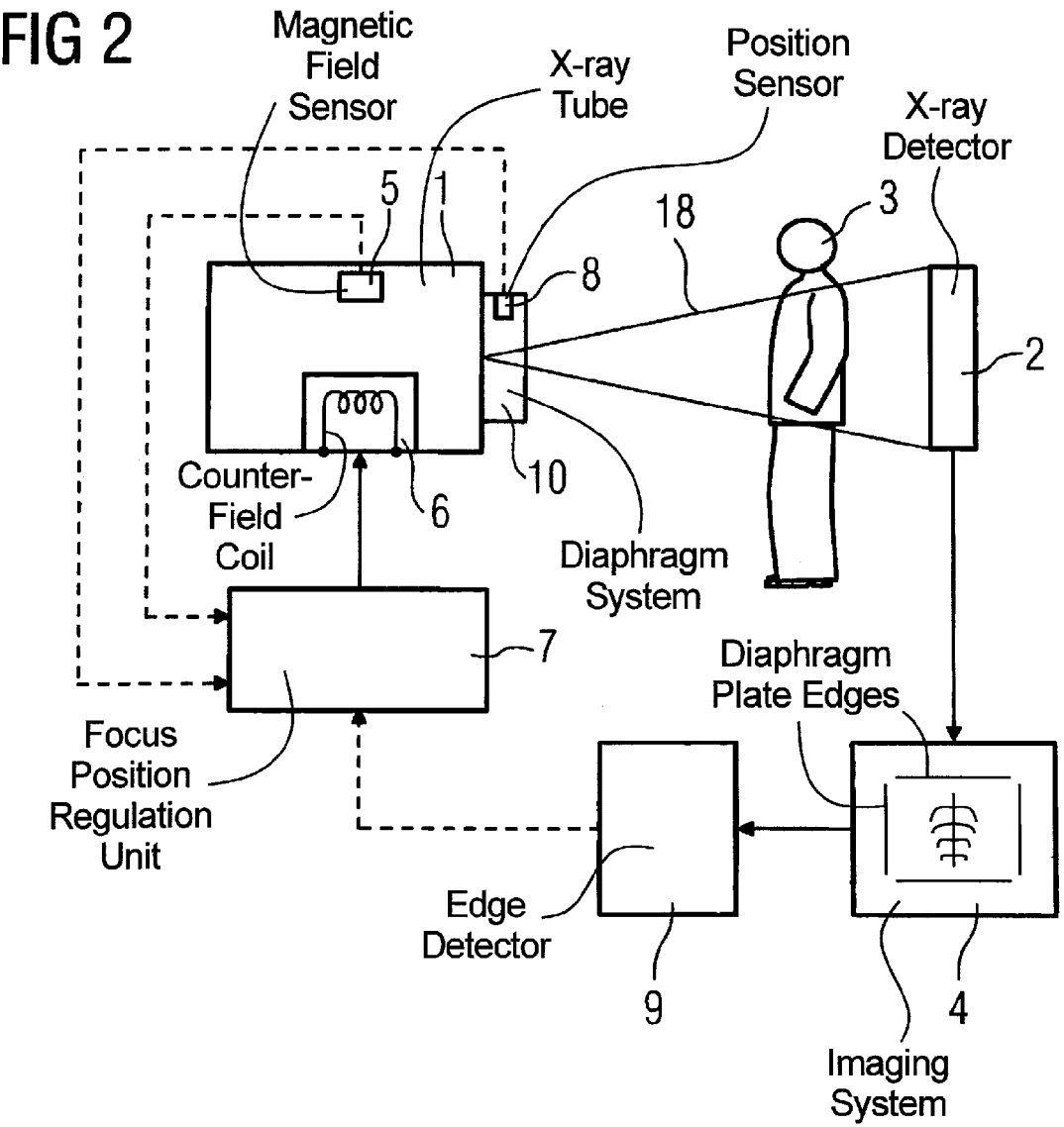
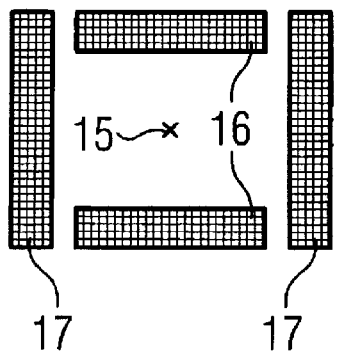

METHOD, X-RAY TUBE AND IMAGING SYSTEM FOR ADJUSTING THE POSITION OF THE X-RAY TUBE FOCUS

BACKGROUND OF THE INVENTION

1. Field of the Invention

The present invention concerns: a method for adjustment of the position of a focus of an x-ray tube, the focus is unwontedly displaced by a magnetic interference field; and an x-ray tube for implementation of such a method, and a medical x-ray acquisition system with an x-ray tube operating according to such a method.

2. Description of the Prior Art

For some years, medical x-ray acquisition systems have been used in connection with magnetic navigation systems for improved control of catheters and guidance wires in blood vessels. Such an overall system composed of a medical x-ray acquisition system and magnetic navigation is known, for example, from the brochure "Axiom Artis dFC Magnetic Navigation" from Siemens Medical Solutions, 2004.

The magnetic field of the navigation system can lead to influences and disruptions of components of the medical x-ray acquisition system such as, for example, the x-ray tube. Typical x-ray tubes are known, for example, from A. Oppelt, "Imaging Systems for Medical Diagnostics", Publicis Corporate Publishing, Erlangen, 2005, page 264 and the following, chapter 12.1, "The x-ray tube". In particular an electron beam that is directed, accelerated onto a rotatable anode plate of the x-ray tube to generate x-ray radiation is very prone to external magnetic interference fields. The electron beam, whose impact point on the anode plate represents the focus point of the x-ray radiation, can be deflected from its intended path by such magnetic interference fields, such that it leads to an unwanted displacement of the position of the focus point and thus to an overall displacement of the generated x-ray beam.

The displacement of the focus position leads to a displacement of the region of the examination subject to be imaged by the x-ray image. Such a displacement is dependent on the distance of the examination subject from the focus, such that the displacement it is greater the closer that the examination subject is to the focus.

In order to reduce the effect of external magnetic interference fields, protective devices for x-ray tubes against are known in the form of ferromagnetic shieldings. Such devices have the disadvantage of exhibiting a high weight and magnetic field strengths in a magnetic field. Primarily in the case of an x-ray apparatus with a moving C-arm or a quickly-rotating gantry, the weight and the magnetic field strength can lead to mechanical deflections and out-of-balances.

SUMMARY OF THE INVENTION

An object of the present invention is to provide a method that minimizes the influence of external magnetic interference fields on the position of the focus of an x-ray tube. Furthermore, it is an object of the invention to provide an x-ray tube as well as an x-ray acquisition system suitable for the implementation of the method.

The object is achieved in accordance with the invention by a method for adjustment of the position of a focus of an x-ray tube wherein the current focus position is corrected on the basis of a determination of the deviation of the current focus position from a target focus position or the determination of a measurement value proportional to the deviation, with the current focus position being adapted to the target focus position by reduction of the deviation or of the measurement value proportional to the deviation. In an embodiment of the invention, in this context it is particularly advantageous to regulate the deviation or the measurement value proportional to the deviation by repeated determination and correction to a value of essentially zero. The influence of external magnetic interference fields on the image quality and the unwanted displacement of the x-ray beam are thereby at least reduced, if not completely eliminated. Ferromagnetic shieldings can be reduced and weight can thus be saved. Less stressing of the mechanism and an interference-free image generation thus result, in particular in x-ray apparatuses with a moving C-arm or a rotating gantry.

A magnetic counter-field which at least reduces the magnetic field strength of the interference field is generated in an advantageous manner for a particularly effective reduction of influences of the interference field, at least at a sub-segment of the electron beam. At least one magnetic field coil or deflection coil preferably is used for generation of this counter-field. The strength of the magnetic field can be variably adjusted by means of such magnetic field coils or deflection coils. The magnetic coils are preferably arranged such that the magnetic field of the interference field can be two-dimensionally compensated.

According to a further embodiment of the invention, the magnetic field strength of the interference field is regulated to a value of essentially zero by regulation of the strength of the counter-field.

The current focus position is measured and compared with the target focus position in an advantageous manner to determine the deviation.

According to a further embodiment of the invention, the measurement value proportional to the deviation is measured. The measurement value proportional to the deviation is advantageously formed from the magnetic field strength of the interference field. The magnetic field strength of the interference field is appropriately measured by a magnetic field sensor. The magnetic field sensor is preferably arranged inside the x-ray tube and optimally close to the electron beam.

According to a further embodiment of the invention, the measurement value proportional to the deviation is formed by the position of the x-ray beam generated from the focus; the current position of the x-ray beam generated from the focus is thus consequently measured. The position of the x-ray beam is measured by a position sensor.

Such position sensors, for example based on x-ray-sensitive semiconductor components, are known and can be integrated simply and cost-effectively into, for example, a diaphragm system associated with the x-ray tube. The position sensor determines the current position of the x-ray beam. If the current position of the x-ray beam is subsequently compared with the target position of the x-ray beam, the deviation of the current focus position from the target focus position is thereby indirectly obtained. However, the impact point of the electron beam on the anode of the x-ray tube, and thus the current focus position, can also be determined by the current position of the x-ray beam. The current focus position can subsequently be compared with a stored target focus position in an evaluation unit. The target focus position can be measured and stored in a calibration in the absence of an interference field.

The measurement value proportional to the deviation can be formed from the position of the shown region on an acquired x-ray image. According to an embodiment of the invention, the position of the shown region on the x-ray image is determined by image processing, in particular by means of detection of the diaphragm edges on the x-ray image. An x-ray detector for acquisition of an x-ray image and an image system for processing and evaluation of the x-ray image are preferably associated with the x-ray tube, and the determination of the measurement value proportional to the deviation is done by the image system, in particular image processing software or an edge detector stored in the image system. According to a further embodiment of the invention, the measurement value proportional to the deviation can be measured by evaluation of an x-ray image with regard to the position of its edges.

BRIEF DESCRIPTION OF THE DRAWINGS

FIG. 2 illustrates an inventive x-ray image acquisition system with a regulation loop for regulation of the focus position.

FIG. 3 shows an arrangement for influencing the electron beam with two coil pairs.

DESCRIPTION OF THE PREFERRED EMBODIMENTS

Figure 1:
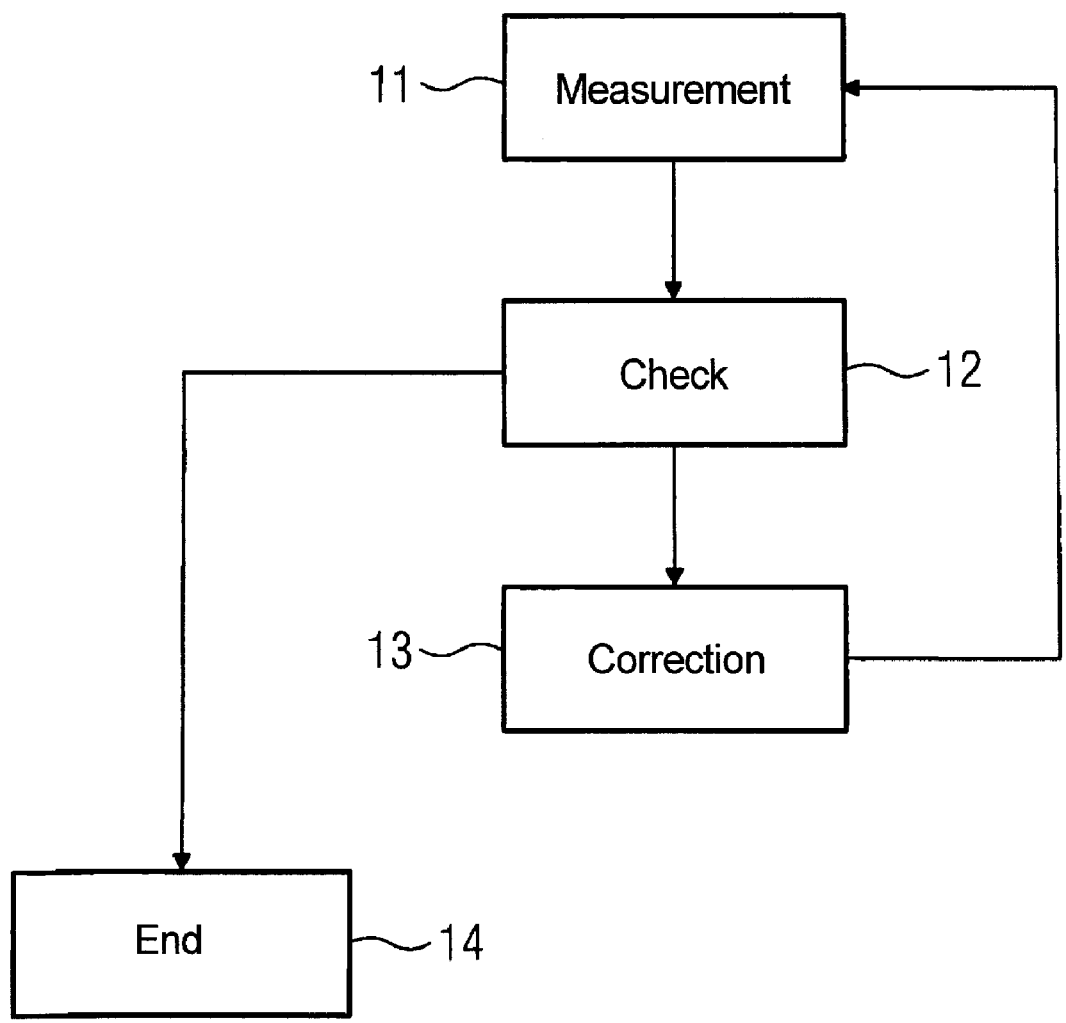
FIG. 1 is a block diagram of an inventive regulation method for adjustment of the position of a focus of an x-ray tube, the focus position being displaced by a magnetic interference field.

A simple workflow of a regulation method according to the invention is shown in FIG. 1 for adjustment of the position of a focus point of an x-ray tube, the focus position being displaced by a magnetic interference field. In a determination step 11, a deviation of a current focus position from a target focus position or a measurement value proportional to the deviation is determined.

For this purpose, at least one measurement is implemented, wherein either the current focus position of the focus point of the x-ray tube or a measurement value that is proportional to the deviation of the current focus position form a target focus position is measured. Such a measurement value can be formed, for example, from the magnetic field strength of the interference field. If the current focus position is measured, this is subsequently compared with the target focus position in order to obtain the deviation of the current focus position from the target focus position.

In a check step 12, the deviation or the measurement value proportional to this is evaluated; this preferably occurs in a regulation unit. Given a deviation or the measurement value proportional to the deviation, the evaluation can be to check whether the deviation or the measurement value exceeds a predetermined threshold. In the check step it is assessed whether steps must be introduced for correction. If the deviation or the measurement value proportional to this exceeds its respective threshold, a measure for reduction of the deviation or of the measurement value proportional to this deviation is taken in a correction step 13.

The determination step 11 for determination of the deviation or of the measurement value proportional to said deviation and subsequently the check step 12 are subsequently repeated. The method is repeated until the deviation or the measurement value proportional thereto falls below its respective, predetermined threshold. Ideally it is regulated until the deviation or the measurement value proportional thereto is essentially zero, represented by an end step 14.

FIG. 2 shows an inventive x-ray image acquisition system with an inventive x-ray tube 1, wherein the respective regulatory connections are schematically shown. A diaphragm system 10 is associated with the x-ray tube 1 and the x-ray image acquisition further has a focus position regulation unit 7, an x-ray detector 2 and an imaging system 4. Such an x-ray image acquisition system also has a control unit (not drawn).

In the x-ray tube 1, an electron beam is generated by a cathode, which electron beam is accelerated onto an anode (in particular a rotating anode). An x-ray beam 18 that can be used for imaging is generated at the impact point of the electron beam on the anode. An examination subject (for example a thorax of a patient 3) is exposed by means of the x-ray beam. The x-ray detector 2, which is preferably a flat panel (planar) image detector, converts the incident x-ray 18 into an x-ray image. The x-ray image can subsequently be processed in the imaging system 4.

The x-ray tube has a magnetic field sensor 5 to determine a magnetic interference field which emanates, for example, from a magnetic navigation system associated with the x-ray image acquisition system. The magnetic field sensor 5 is preferably arranged on or in the vacuum housing of the x-ray tube 1; the magnetic field sensor 5 preferably exhibits an optimally small distance from the electron beam.

For compensation of the interference field, the x-ray tube 1 has a counter-field generator in the form of at least one counter-field coil 6. The counter-field coil 6 is activated by the focus position regulation unit 7 and can be adapted in terms of its magnetic field strength, which is indicated by the connection arrow between the counter-field coil and the focus position regulation unit 7.

Moreover, the inventive x-ray image acquisition system has at least one position sensor 8 that is preferably arranged in the diaphragm system 10. The position sensor 10 is fashioned to measure the current focus position of the focus point. The position sensor 8 and/or the magnetic field sensor 5 are connected with the focus position regulation unit 7 such that they communicate their respective measurement values to the focus position regulation unit 7. Alternatively, one or more units measuring the current focus position or the proportional measurement value can be present in the inventive x-ray acquisition system, thus for example only one position sensor 8 or only one magnetic field sensor or both. The focus position regulation unit 7 controls the counter-field coil 6 or its magnetic field based on the measurement values.

For example, the magnetic field sensor 5 can measure the interference field and communicate the measurement value to the focus position regulation unit 7. This controls the counter-field coil 6 to develop a counter-field via which the interference field is reduced in the region of the electron beam. The magnetic field sensor in turn measures the current interference field and communicates the measurement value to the focus position regulation unit 7, which in turn activates the counter-field coil. In this manner the interference field can be regulated to a value of essentially zero in the relevant region and the influence of the interference can thus be minimized.

A regulation on the basis of the deviation of the current focus position from the target focus position can likewise be provided. The position sensor 8, for example an x-ray-sensitive semiconductor sensor, measures the position of the x-ray beam and determines from this the current focus position. The current focus position is then communicated to the focus position regulation unit 7, which compares the current focus position with the target focus position and determines the deviation. The focus position regulation unit 7 controls the counter-field coil 6 on the basis of the deviation. The position sensor 8 subsequently newly determines the current focus position and transmits it. This method is continued until the deviation is essentially zero. The position sensor 8 can also directly communicate the current position of the x-ray beam.

Regulation can likewise be provided on the basis of the position of the diaphragm edges of the diaphragm system 10 in the x-ray image. In the case of regulation on the basis of the position of the diaphragm edges in the x-ray image, an x-ray image is acquired by the x-ray detector 2 and the position of the diaphragm edges is determined by image processing software in the image system in the form of an edge detector 9. This measurement value is relayed from the edge detector 9 to the focus position regulation unit 7.

The target focus position or the proportional measurement value can be determined in the absence of magnetic interference fields. This can be implemented, for example, once upon startup of the x-ray tube or regularly in the framework of a recalibration. The values so determined can be subsequently used as references for the deviation of the current focus position given the presence of magnetic interference fields.

FIG. 3 shows a generator for generation of the counter-field in the form of two Helmholtz coil pairs 16 and 17 whose respective magnetic fields are arranged perpendicular to one another and perpendicular to the path of the electron beam 15. Helmholtz coils generate a particularly uniform magnetic field internally. A complete two-dimensional compensation of the components of the magnetic interference field that influence the electron beam 15 is possible with such an arrangement.

A known magnetic electron beam deflection system as in A. Oppelt, "Imaging Systems for Medical Diagnostics", Publicis Corporate Publishing, Erlangen, 2005, page 281, section 12.19, described therein for generation of a counter-field, can also be used as well.

The x-ray acquisition system can be formed, for example, by an angiography x-ray apparatus with a movable C-arm or by a computed tomography apparatus with a gantry rotating around an examination subject.

The invention can be briefly summarized as follows. In order to reduce the influence of magnetic interference fields on the position of an x-ray focus of an x-ray tube, a method is provided for adjustment of the focus position of the focus point of the x-ray tube (which focus position is displaced by a magnetic interference field) that includes determination of the deviation of a current focus position from a target focus position or of a measurement value proportional to the deviation, correction of the focus position, by reducing the deviation of the current focus position from the target focus position, or a measurement value proportional to the deviation, on the basis of the determined deviation or the determined measurement value proportional to the deviation.

In an embodiment of the invention, the deviation of the current focus position from the target focus position or the measurement value proportional to the deviation is regulated to a value of essentially zero by repeated determination and correction.

Although modifications and changes may be suggested by those skilled in the art, it is the intention of the inventors to embody within the patent warranted hereon all changes and modifications as reasonably and properly come within the scope of their contribution to the art.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for adjusting a position of a focus in an x-ray tube, comprising the steps of:
   emitting an x-ray beam from an x-ray tube by emitting an electron beam from a cathode in the x-ray tube that strikes an anode in the x-ray tube at a current focus position from which the x-ray beam is emitted, said current focus position deviating from a target focus position on the anode due to an interfering magnetic field;
   gating said x-ray beam with a diaphragm comprised of diaphragm plates having diaphragm edges, to produce a gated x-ray beam;
   detecting x-rays in said gated x-ray beam with an x-ray detector;
   in an imaging computer, generating an x-ray image from the x-rays detected by said detector, said x-ray image including said diaphragm plates; and
   in a processor, automatically determining a deviation of said current focus position in the x-ray tube from the target focus position in the x-ray tube by determining a deviation value by evaluating respective positions of the edges of said diaphragm plates in said x-ray image; and
   automatically electronically correcting said current focus position by reducing the deviation of said current focus position from said target focus position dependent on said deviation value.

2. A method as claimed in claim 1 comprising determining said deviation value repeatedly and regulating said deviation value to produce a regulation value of substantially zero.

3. A method as claimed in claim 1 comprising reducing said deviation value by generating a counter magnetic field that counters an effect of said interfering magnetic field.

4. A method as claimed in claim 3 comprising regulating a strength of said counter magnetic field to produce a deviation value of substantially zero.

5. A method as claimed in claim 3 comprising generating said counter magnetic field with a magnetic field coil.

6. A method as claimed in claim 1 comprising determining at least one of the target focus position or said deviation value with no deviation of the current focus position from the target position as a calibration with no magnetic interference field being present.

7. A medical x-ray image acquisition system comprising:
   an x-ray tube comprising a cathode that emits an electron beam, and an anode struck by the electron beam at a current focus position from which an x-ray beam is emitted, said current focus position deviating from a target focus position on the anode due to an intervening magnetic field;
   a diaphragm system disposed in a path of said x-ray beam that gates said x-ray beam with diaphragm plates, to produce a gated x-ray beam;
   an x-ray detector that detects x-rays in said x-ray gated beam;
   an imaging computer connected to said x-ray detector that generates an x-ray image from the x-rays detected by said detector, said x-ray image including said diaphragm plates;
   a processor that determines a deviation of said current focus position in the x-ray tube from a target focus position in the x-ray tube by determining a deviation value by evaluating respective positions of edges of said diaphragm plates in said x-ray image; and
   a focus position regulator supplied with said deviation value that corrects the current focus position by reducing the deviation of said current focus position from said target focus position dependent on the deviation value.

* * * * *